United States Patent
Adorni Pereira

(10) Patent No.: US 12,112,834 B2
(45) Date of Patent: Oct. 8, 2024

(54) SYSTEM AND METHOD FOR NON-INVASIVE QUANTIFICATION OF BLOOD BIOMARKERS

(71) Applicant: Refana Inc., Las Vegas, NV (US)

(72) Inventor: Marcelo Adorni Pereira, Charneca da Caparica (PT)

(73) Assignee: Refana, Inc., Las Vegas, NV (US)

( * ) Notice: Subject to any disclaimer, the term of this patent is extended or adjusted under 35 U.S.C. 154(b) by 0 days.

(21) Appl. No.: 18/358,655

(22) Filed: Jul. 25, 2023

(65) Prior Publication Data
US 2024/0079093 A1 Mar. 7, 2024

Related U.S. Application Data

(63) Continuation of application No. 17/929,804, filed on Sep. 6, 2022, now Pat. No. 11,742,059.

(51) Int. Cl.
| | |
|---|---|
| G16B 40/10 | (2019.01) |
| G01N 33/49 | (2006.01) |
| G06F 18/214 | (2023.01) |
| G06N 20/00 | (2019.01) |

(52) U.S. Cl.
CPC ............ G16B 40/10 (2019.02); G01N 33/49 (2013.01); G06F 18/214 (2023.01); G06N 20/00 (2019.01); *G01N 2800/60* (2013.01)

(58) Field of Classification Search
CPC .... G16B 40/10; G01N 33/49; G01N 2800/60; G06F 18/214; G06N 20/00
See application file for complete search history.

(56) References Cited

U.S. PATENT DOCUMENTS

| | | | | |
|---|---|---|---|---|
| 6,280,381 | B1 * | 8/2001 | Malin | G01N 21/49 |
| | | | | 128/920 |
| 10,339,464 | B2 * | 7/2019 | Martin | G16B 40/00 |
| 10,815,518 | B2 * | 10/2020 | Martins | C12Q 1/6841 |

(Continued)

FOREIGN PATENT DOCUMENTS

WO 00/42907 A 7/2000

OTHER PUBLICATIONS

Burns, D. H. et al. "Near-infrared spectroscopy of blood plasma for diagnosis of sporadic Alzheimer's disease". Journal of Alzheimer's Disease, pp. 391-397, 2009.

*Primary Examiner* — Roy M Punnoose
(74) *Attorney, Agent, or Firm* — Vorys, Sater, Seymour and Pease LLP; Anthony P. Venturino; Maryellen Feehery Hank

(57) ABSTRACT

A system, method for determining blood biomarkers implemented by a processor and memory circuitry (PMC) and a program storage device and computer program product which includes providing near infra-red spectrogram data i of a patient's living tissue; using one or more pre-trained prediction models comprising a selected number of prediction routes, and determining prediction data on a selected group of biomarkers; determining one or more biomarkers associated with a number of groups, and determining an average concentration data of said biomarkers in accordance with output data of a number of prediction routes associated with said number of groups; and generating output data indicative of estimated levels of a selected set of biomarkers for said patient.

15 Claims, 8 Drawing Sheets

(56) References Cited

U.S. PATENT DOCUMENTS

| | | |
|---|---|---|
| 2006/0281982 A1 | 12/2006 | Grata et al. |
| 2008/0117416 A1 | 5/2008 | Hunter et al. |
| 2014/0187519 A1* | 7/2014 | Cooke ................ G01N 33/6893 514/263.36 |
| 2017/0188818 A1 | 7/2017 | Yi et al. |
| 2018/0037929 A1* | 2/2018 | Martins .............. A61B 5/14546 |
| 2020/0323484 A1* | 10/2020 | Aronovich .............. G10L 17/02 |
| 2022/0257149 A1* | 8/2022 | Ralston ................. G16H 50/50 |
| 2022/0323019 A1* | 10/2022 | Arcot Desai ........ A61B 5/4848 |

\* cited by examiner

| n | 1 | 2 | 3 | ... | 55 | 56 | ... | 1559 | 1560 |
|---|---|---|---|---|---|---|---|---|---|
| Rflx1 | 0.09058 | 0.1064 | 0.1076 | ... | 0.6398 | 0.9435 | ... | 0.3304 | 0.3157 |
| . | . | . | . |  | . | . |  | . | . |
| . | . | . | . | ... | . | . | ... | . | . |
| . | . | . | . |  | . | . |  | . | . |
| Rflxk | 0.1009 | 0.09170 | 0.1075 | ... | 0.6408 | 0.9419 | ... | 0.3401 | 0.3149 |
| Wave | 650nm | 780nm | 950nm | ... | 1745nm | 1787nm | ... | 1360nm | 2450nm |

FIG. 2A $$S = \begin{bmatrix} 0.1058 & 0.1064 & 0.1076 & \cdots & 0.3398 & 0.3435 & \cdots & 0.3304 & 0.3157 \\ \vdots & \vdots & \vdots & \cdots & \vdots & \vdots & \cdots & \vdots & \vdots \\ 0.1049 & 0.1070 & 0.1075 & \cdots & 0.3408 & 0.3419 & \cdots & 0.3401 & 0.3149 \end{bmatrix} \quad B = [b1, b2, b3, \vdots, bn]$$

FIG. 2B

SYSTEM AND METHOD FOR NON-INVASIVE QUANTIFICATION OF BLOOD BIOMARKERS

TECHNOLOGICAL FIELD

The present disclosure relates to analysis of blood biomarkers, and specifically relates to analysis of blood biomarkers based on spectrometric measurements using one or more prediction models.

BACKGROUND

Analysis of blood biomarkers is one of the most widely used medical tests. The blood generally includes a plurality of biomarkers that provide valuable information on an individual's general health. To obtain data on blood biomarkers, a clinical specialist/physician typically draws a blood sample from an individual's vein, and the blood sample is transmitted to be tested in a laboratory, to obtain quantitative data on the individual's blood biomarkers.

Various techniques have been described for simplifying the blood testing process. Such techniques include generally various techniques that relate to chemical testing of the blood sample, as well as the use of one or more prediction models to obtain data on one or more biomarkers.

U.S. Pat. No. 10,815,518 describes a sampler and a method of parameterization by calibration of digital circuits and non-invasive determination of the concentration of several biomarkers, simultaneously and in real time. The method makes use of equipment which, from a set of luminous signatures-spectrum-provided by a spectrophotometer (E5) (E6), applies a digital filter that breaks down the spectrum into sub-spectra that shows the digital signatures of relevant markers and, through a digital decoder, the concentration of a set of several biomarkers is obtained simultaneously and in real time.

US 2006/281982 discloses an apparatus for non-invasive sensing of biological analytes in a sample, which includes an optics system having at least one radiation source and at least one radiation detector; a measurement system operatively coupled to the optics system; a control/processing system operatively coupled to the measurement system and having an embedded software system; a user interface/peripheral system operatively coupled to the control/processing system for providing user interaction with the control/processing system; and a power supply system operatively coupled to the measurement system, the control/processing system and the user interface system for providing power to each of the systems. The embedded software system of the control/processing system processes signals obtained from the measurement system to determine a concentration of the biological analytes in the sample.

GENERAL DESCRIPTION

Testing for blood biomarkers is one of the first medical tests conducted by any physician for the purpose of medical diagnosis. Although being simple and routine, the procedure of drawing blood from a patient requires certain skill, and may raise stress levels for some patients. Further, laboratory testing of blood samples is a process that takes time, and results may be provided only 1-2 days after the test.

Accordingly, there is a need in the art for a blood biomarker testing technique that solves the above issues. The present disclosure provides a technique for quantifying one, or more, and generally a selected plurality of blood biomarkers, by processing spectrometric reading from a patient's tissue (e.g., skin) to determine a prediction of blood biomarker levels. The present technique utilizes generating a selected number of groups of biomarkers, each including two or more biomarkers, and generating a respective prediction route for each group. The selected set of groups of biomarkers is determined in accordance with one or more biomarker characterization parameters. Generally, the biomarkers may be selected in groups in accordance with typical concentration levels, and/or respective measures of the effect of the biomarkers on spectrographic data. Each group includes two or more biomarkers characterized by typical high concentration, and a biomarker characterized by low concentration level. The concentration may be determined by the number of particles per blood volume, where high concentration may be determined as greater than a first threshold (e.g., between 5% and 20%, in some embodiments about 10% of blood composition by number of particles), and low concentration may be determined as lower than a second threshold (e.g., lower than 5% by number of particles, or lower than 3%). The concentration level may be weighted by typical spectral absorption of the biomarkers, such that biomarkers having high absorption may be considered as associated with increased typical concentration. According to some embodiments, selected biomarkers, typically being frequently measured, or high impact biomarkers, may be included in two or more groups, thereby enhancing prediction of respective concentration for these selected biomarkers. In some embodiments, all biomarkers may be included in two or more groups. Arrangement of the biomarkers in groups, and determining a prediction model for prediction of groups of biomarkers, may enhance accuracy of the prediction model, and may overcome issues associated with overfitting of the prediction model to the training data set. Grouping of biomarkers based on typical concentration levels, where a group generally includes two or more biomarkers characterized by high concentration, and one or more biomarkers characterized by low concentration, may provide an anchor for the prediction model, enhancing sensitivity to variations in biomarker concentration and the effect thereof on the spectrogram data used as input to the prediction model.

To this end, the present disclosure provides a technique for generating at least a prediction model, operable using a processor and memory circuitry (PMC). The PMC is operative to generate and/or implement at least one prediction model as described herein. More specifically, the PMC is configured to receive input data being a training data set for training said at least one prediction model to determine blood biomarkers data in accordance with spectrogram data obtained from a patient's skin.

Using a plurality of spectrograms obtained from a plurality of individuals, and labeled by respective data on blood biomarker levels, the present disclosure provides a technique for generating one or more prediction models. To provide improved accuracy, the present technique utilizes grouping the list of desired biomarkers into a selected number of groups, such that at least a selected number of biomarkers are included in two or more (preferably three or more) of the groups of biomarkers. This technique enables prediction of the selected number of biomarkers through two or more prediction routes, thus enhancing prediction accuracy over conventional techniques.

Thus, according to a first broad aspect, the present disclosure provides a method implemented by a processor and memory circuitry (PMC), the method comprising:

(a) providing a training data set, said training data set comprising one or more spectrogram data pieces obtained from a plurality of individuals and respective data on a selected set of blood biomarkers of said individuals;
(b) selecting one or more groups of biomarkers selected from said selected set of biomarkers, wherein each group includes two or more (three or more) biomarkers;
(c) training one or more prediction models based on said training data, said one or more prediction models comprising one or more prediction routes for prediction of said one or more groups of biomarkers respectively; thereby providing a prediction model comprising one or more prediction routes, each trained for predicting data on respective groups of said one or more groups of biomarkers.

According to some embodiments, said selecting one or more groups of biomarkers comprises selecting said one or more groups, wherein at least a selected number of biomarkers are associated with two or more groups.

According to some embodiments, said selecting one or more groups of biomarkers comprises pairing two or more biomarkers characterized by typical concentration above a first threshold, and one or more biomarkers characterized by typical concentration below a second threshold.

According to some embodiments, said concentration may be determined by the amount of biomarker particles as a percentage of typical blood composition.

According to some embodiments, said selecting one or more groups of biomarkers comprises pairing two or more biomarkers characterized by typical spectral effect above a first threshold, and one or more biomarkers characterized by typical spectral effect below a second threshold.

According to some embodiments, said spectral effect is determined by the typical amount of biomarkers as a percentage of blood composition, and typical height of spectral signature of said biomarker.

According to some embodiments, said first threshold is indicative of between 5% and 20% of blood composition, said second threshold being lower or equal to said first threshold. For example, the first threshold may be about 10%, or about 15%, or about 20%, or about 5%.

According to some embodiments, said spectrogram data obtained from a plurality of individuals comprises a plurality of spectrogram readings collected within a selected timeframe associated with blood circulation of a selected portion of an individual's blood volume.

According to some embodiments, said spectrogram data is indicative of wavelengths within a range between 600-2700 nm.

According to some embodiments, said training one or more prediction models comprises:
(a) using a first portion of the training data set for calibration of said one or more prediction models to identify one or more biomarker groups based on spectrogram input data;
(b) using a second portion of the training data set for validating said one or more prediction models;
(c) using a third portion of the training data set for testing said one or more prediction models;
(d) repeating training if either one of validating or testing of at least one of said one or more prediction models indicates accuracy below a selected threshold.

According to some embodiments, said repeating training comprises reshuffling said first and second portions of the training data set to repeat training. According to some embodiments, should testing of at least one of said one or more prediction models indicate accuracy below a selected threshold, said repeating training comprises providing an additional training data set.

According to a second broad aspect, the present disclosure provides a program storage device readable by machine, tangibly embodying a program of instructions executable by the machine to perform a method comprising:
(a) providing a training data set, said training data set comprising one or more spectrogram data pieces obtained from a plurality of individuals and respective data on a selected set of blood biomarkers of said individuals;
(b) selecting one or more groups of biomarkers selected from said selected set of biomarkers, wherein each group includes two or more (three or more) biomarkers;
(c) training one or more prediction models based on said training data, said one or more prediction models comprising one or more prediction routes for prediction of said one or more groups of biomarkers respectively; providing a prediction model comprising one or more prediction routes each trained for predicting data on respective groups of said one or more groups of biomarkers.

According to some embodiments, said selecting one or more groups of biomarkers comprises: pairing two or more biomarkers characterized by typical concentration above a first threshold and one or more biomarkers characterized by typical concentration below a second threshold, or pairing two or more biomarkers characterized by typical spectral effect above a first threshold, and one or more biomarkers characterized by typical spectral effect below a second threshold.

According to some embodiments, the program storage device may comprise computer readable instructions as indicated in embodiments of the first broad aspect.

According to a third broad aspect, the present disclosure provides a computer program product comprising a computer useable medium having computer readable program code embodied therein, the computer program product comprising computer readable program code for causing the computer to:
provide a training data set, said training data set comprising one or more spectrogram data pieces obtained from a plurality of individuals and respective data on a selected set of blood biomarkers of said individuals;
select one or more groups of biomarkers selected from said selected set of biomarkers, wherein each group includes two or more (three or more) biomarkers;
train one or more prediction models based on said training data, said one or more prediction models comprising one or more prediction routes for prediction of said one or more groups of biomarkers respectively;
provide a prediction model comprising one or more prediction routes, each trained for predicting data on respective groups of said one or more groups of biomarkers.

According to some embodiments, said computer readable program code for causing the computer to select one or more groups of biomarkers comprises instructions for selecting one or more groups of biomarkers by pairing two or more biomarkers characterized by typical concentration above a first threshold, and one or more biomarkers characterized by typical concentration below a second threshold, or pairing two or more biomarkers characterized by typical spectral effect above a first threshold, and one or more biomarkers characterized by typical spectral effect below a second threshold.

According to some embodiments, the computer readable program code may comprise computer readable program code for causing the computer to perform method operations as indicated in embodiments of the first broad aspect.

According to a fourth broad aspect, the present disclosure provides a method for determining blood biomarkers implemented by a processor and memory circuitry (PMC), comprising:
(a) providing spectrogram data indicative of near infra-red absorption of a patient's tissue;
(b) using one or more pre-trained prediction models comprising a selected number of prediction routes, and determining prediction data on a selected group of biomarkers;
(c) determining one or more biomarkers associated with a number of groups and determining an average concentration data of said biomarkers in accordance with output data of a number of prediction routes associated with said number of groups; and
(d) generating output data indicative of estimated levels of a selected set of biomarkers for said patient.

According to some embodiments, said providing spectrogram data comprises providing spectrogram data in a range between 600 nm and 2700 nm.

According to some embodiments, said providing spectrogram data comprises obtaining spectrometric reading of a patient's living tissue, for example from said patient's skin.

According to some embodiments, said selected number of prediction routes comprises prediction routes pre-trained for predicting data on selected groups of biomarkers, being different between said prediction routes.

According to some embodiments, said selected groups of biomarkers comprise a selected number of groups, each group comprising two or more biomarkers characterized by a typical concentration above a first threshold, and one or more biomarkers characterized by a typical concentration below a second threshold.

According to a fifth broad aspect, the present disclosure provides a program storage device readable by machine, tangibly embodying a program of instructions executable by the machine to perform a method for determining blood biomarkers, comprising:
(a) providing spectrogram data indicative of near infra-red absorption of a patient's tissue;
(b) using one or more pre-trained prediction models comprising a selected number of prediction routes, and determining prediction data on a selected group of biomarkers;
(c) determining one or more biomarkers associated with a number of groups and determining an average concentration data of said biomarkers in accordance with output data of a number of prediction routes associated with said number of groups; and
generating output data indicative of estimated levels of a selected set of biomarkers for said patient.

According to some embodiments, said selected groups of biomarkers comprise a selected number of groups, each group comprising two or more biomarkers characterized by typical concentration above a first threshold, and one or more biomarkers characterized by typical concentration below a second threshold.

According to some embodiments, the program storage device may comprise computer readable instructions as indicated in embodiments of the fourth broad aspect.

According to a sixth broad aspect, the present disclosure provides a computer program product comprising a computer useable medium having computer readable program code embodied therein for determining blood biomarkers, the computer program product comprising computer readable program code for causing the computer to:
provide spectrogram data indicative of near infra-red absorption of a patient's tissue;
use one or more pre-trained prediction models comprising a selected number of prediction routes and determining prediction data on a selected group of biomarkers;
determine one or more biomarkers associated with a number of groups, and determine an average concentration data of said biomarkers in accordance with output data of a number of prediction routes associated with said number of groups; and
generate output data indicative of estimated levels of a selected set of biomarkers for said patient.

According to some embodiments, said selected groups of biomarkers comprise a selected number of groups, each group comprising two or more biomarkers characterized by typical concentration above a first threshold, and one or more biomarkers characterized by typical concentration below a second threshold.

According to some embodiments, the computer readable program code may comprise computer readable program code for causing the computer to perform method operations as indicated in embodiments of the fourth broad aspect.

According to a seventh broad aspect, the present disclosure provides a system comprising a processor and memory circuitry (PMC), wherein the PMC is configured to:
(a) obtain a training data set, said training data set comprising one or more spectrogram data pieces obtained from a plurality of individuals and respective data on a selected set of blood biomarkers of said individuals;
(b) select one or more groups of biomarkers selected from said selected set of biomarkers, wherein each group includes two or more (three or more) biomarkers;
(c) train one or more prediction models based on said training data, said one or more prediction models comprise one or more prediction routes for prediction of said one or more groups of biomarkers respectively;
thereby providing a prediction model comprising one or more prediction routes, each trained for predicting data on respective groups of said one or more groups of biomarkers.

According to some embodiments, said PMC is configured to select one or more groups of biomarkers, comprising selecting said one or more groups, wherein at least a selected number of biomarkers are associated with two or more groups.

According to some embodiments, said PMC is configured to select one or more groups of biomarkers comprising pairing two or more biomarkers characterized by typical concentration above a first threshold, and one or more biomarkers characterized by typical concentration below a second threshold.

According to some embodiments, said concentration is determined by amount of biomarker particles as a percentage of typical blood composition.

According to some embodiments, said PMC is configured to select one or more groups of biomarkers comprising pairing two or more biomarkers characterized by typical spectral effect above a first threshold, and one or more biomarkers characterized by typical spectral effect below a second threshold.

According to some embodiments, said spectral effect is determined by typical amount of biomarkers as a percentage of blood composition, and typical height of spectral signature of said biomarker.

According to some embodiments, said first threshold is indicative of 5%, or 10%, or 15%, or 20%, of blood composition, said second threshold being lower or equal to said first threshold.

According to some embodiments, said spectrogram data obtained from a plurality of individuals comprises a plurality of spectrogram readings collected within a selected timeframe associated with blood circulation of a selected portion of an individual blood volume.

According to some embodiments, said spectrogram data is indicative of spectral absorption within a range between 600-2700 nm.

According to some embodiments, said PMC is configured to train said one or more prediction models by:
(a) using a first portion of the training data set for calibration of said one or more prediction models to identify one or more biomarker groups based on spectrogram input data;
(b) using a second portion of the training data set for validating said one or more prediction models;
(c) using a third portion of the training data set for testing said one or more prediction models;
(d) repeating training if either one of validating or testing of at least one of said one or more prediction models indicates accuracy below a selected threshold.

According to some embodiments, said PMC is configured to reshuffle said first and second portions of the training data set to repeat training.

According to an eighth broad aspect, the present disclosure provides a system for non-invasive determining of blood biomarkers comprising a processor and memory circuitry (PMC), wherein the PMC comprises a pre-stored prediction model and is configured to:
(a) obtain spectrogram data indicative of near infra-red absorption of a patient's tissue;
(b) use one or more pre-trained prediction models comprising a selected number of prediction routes, and determining prediction data on a selected group of biomarkers;
(c) determine one or more biomarkers associated with a number of groups and determine an average concentration data of said biomarkers in accordance with output data of a number of prediction routes associated with said number of groups; and
(d) generate output data indicative of estimated levels of a selected set of biomarkers for said patient.

According to some embodiments, the system may further comprise at least one spectrometer connectable to said PMC for transmission of communication signals, said at least one spectrometer being configured for obtaining spectrogram data from biological tissue.

According to some embodiments, said at least one spectrometer is configured to obtain spectrogram data from the skin of an individual.

According to some embodiments, said at least one spectrometer is configured to obtain spectrogram data comprising a spectral range between 600 nm and 2700 nm.

According to some embodiments, said selected number of prediction routes comprise prediction routes pre-trained for predicting data on selected groups of biomarkers, being different between said prediction routes.

According to some embodiments, said selected groups of biomarkers comprise a selected number of groups, each group comprising two or more biomarkers characterized by typical concentration above a first threshold, and one or more biomarkers characterized by typical concentration below a second threshold.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A and 2B exemplify input data in the form of spectrogram data (FIG. 2A) and spectrogram data labeled by blood biomarker data (FIG. 2B);

FIG. 8A illustrates a possible arrangement of biomarkers in a hypothetical solution domain, FIG. 8B illustrates expected divergence tendency associated with an optimization step following the state in FIG. 8A, FIG. 8C illustrates a possible arrangement of groups of biomarkers in a solution domain according to some embodiments of the present disclosure, and FIG. 8D exemplifies expected convergence tendency associated with an optimization step following the state in FIG. 8C according to some embodiments of the present disclosure.

DETAILED DESCRIPTION OF EMBODIMENTS

Figure 1:
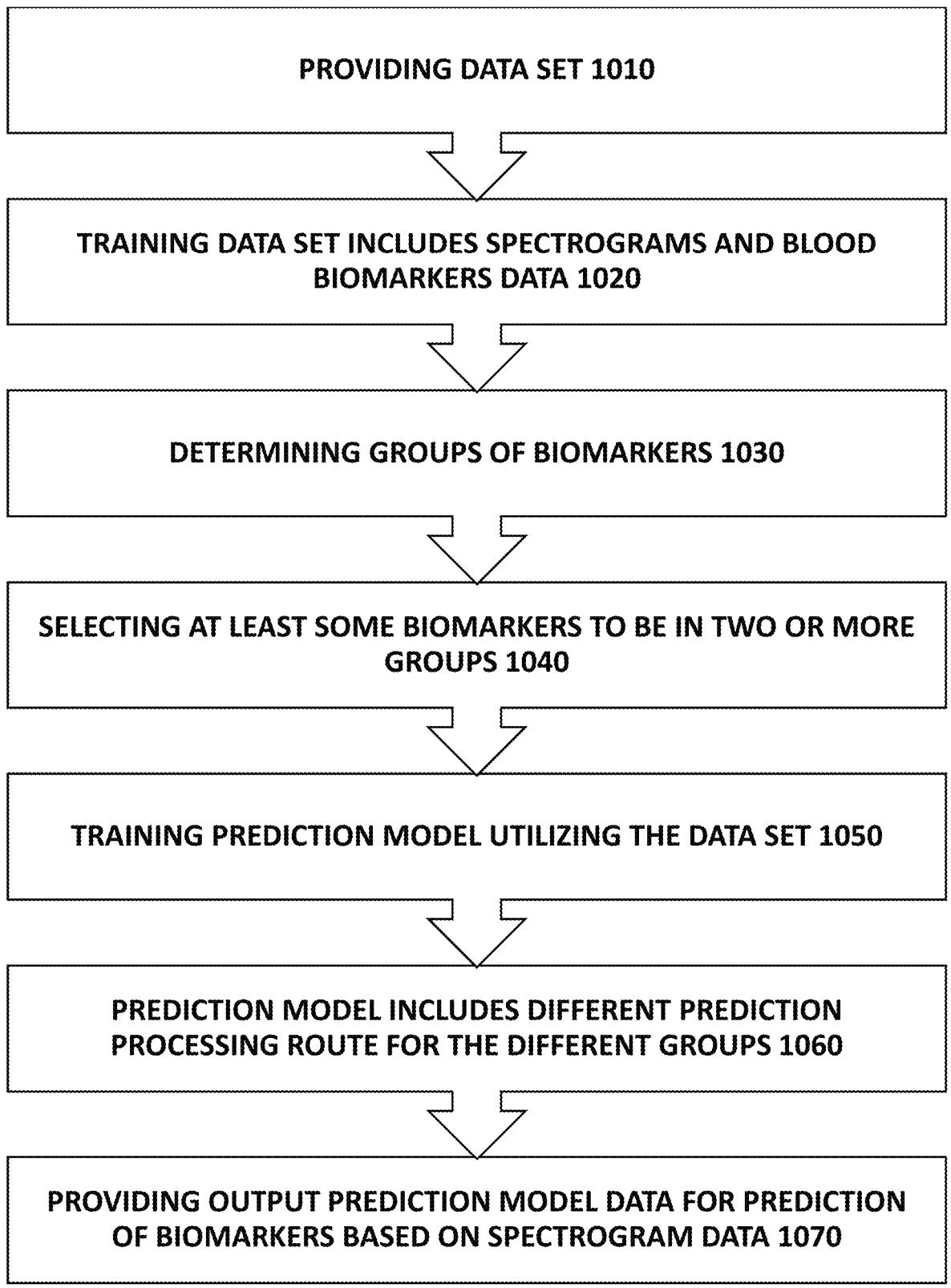
FIG. 1 illustrates a method for generating a prediction model for blood biomarkers according to some embodiments of the present disclosure.

As indicated above, the present disclosure provides a technique of generating a prediction model for determining biomarkers based on spectrometric readings from a patient's tissue, and a technique for using such a prediction model in determining a patient's blood biomarkers levels.

In this connection, the term 'blood biomarkers' as used herein relates to any molecule, macromolecule, or cluster of molecules, that is, or may be present, in an individual's blood, and may be a target for blood test analysis. The term blood biomarker may be used herein in combination with additional terms, such as marker, analyte, bio-analyte, and molecule, as used herein below.4

Unless specifically stated otherwise, as apparent from the following discussions, it is appreciated that throughout the specification, discussions utilizing terms such as "obtaining", "using", "feeding", "determining", "estimating", "generating" or the like, refer to the action(s) and/or process(es) of a computer that manipulate and/or transform data into other data, said data represented as physical, such as electronic, quantities and/or said data representing the physical objects.

The terms "computer" or "computerized system" should be expansively construed to include any kind of hardware-based electronic device with a data processing circuitry (e.g., digital signal processor (DSP), a GPU, a TPU, a field programmable gate array (FPGA), an application specific integrated circuit (ASIC), microcontroller, microprocessor etc.). The processing circuitry can comprise, for example, one or more processors operatively connected to computer memory, loaded with executable instructions for executing operations, as further described below. The processing circuitry encompasses a single processor or multiple processors, which may be located in the same geographical zone or may, at least partially, be located in different zones, and may be able to communicate together.

The present technique utilizes input data in the form of spectrogram data collected from a patient's/user's/individual's tissue. For example, the spectrogram may be collected using an optical spectrometer from an individual's skin, e.g., wrist, fingertip, forehead, arms, neck, chest, cheeks, legs, etc. Generally, body regions having high capillary blood flow or high capillary density may be preferred. The spectrogram data may be collected within an infrared portion of the electromagnetic spectrum, including wavelengths in the range between 600-2700 nm, or between 800-2700 nm. Generally, the present technique may be relevant for any range of wavelengths in which spectrogram data is obtained and is used for training the prediction model as described herein below. Moreover, a spectrometer may be configured to obtain spectrogram data within a broader range. Such a spectrometer may also be suitable, while ranges, for which the prediction model is prepared, are used in analysis.

The term infrared, or near infrared (NIR), as used herein, relates to portions of the electromagnetic spectrum commonly known as infrared or near infrared. It should however be noted that the present technique may, in general, be used with other spectral ranges including e.g., visible spectrum, mid-infrared, and/or far infrared wavelength ranges. Typically, the near infrared spectrum in the range of 600-2700 nm, or 600-2000 nm, or 700-2000, or 700-2700 nm, or 800-2000 nm, or 800-2700 nm, is preferred for analysis of biomarkers, due to absorbance by functional groups characterizing biochemical compounds.

For example, the spectrogram data may include data on spectral absorbance/reflection within the selected range, using spectral resolution between 2 and 60 nm. As indicated herein, the spectrogram data may be acquired throughout a selected period of time, where a plurality of spectrograms are collected within a period of 1-10 minutes. Accordingly, a set of spectrogram data from an individual may include a plurality of spectrograms, each assigned with time of acquisition. The set of spectrograms may be averages to determine and average spectrogram readout of an individual.

The spectrogram data collected from an individual typically includes a list of absorption levels (often presented in a graph) indicating level of absorption of the individual tissue for different wavelengths within the selected range. The present technique preferably utilizes spectrogram data that includes a plurality of spectroscopic measurements obtained from the tissue of the user within a selected measurement time (e.g., 2-180 seconds). Typically, collection of spectrogram data may take about 1 second, such that within the selected measurement time, a plurality of spectrogram measurements may be collected. The plurality of spectrogram measurements may vary in accordance with blood circulation through the individual's blood vessels, such that within a measurement time of about 90 seconds, the spectrogram measurements are indicative of entire blood volume circulating through the individual's body. Further, in some embodiments, collecting of spectrogram data for training of the prediction models as described herein below, may be performed within a selected measurement time. The so-collected plurality of spectrograms may be further analyzed for consistency, e.g., by determining standard variation of the spectrogram data between the different spectral measurements; spectrogram data pieces having standard deviation that exceeds a preselected threshold, may be determined as inconsistent, and thus may be omitted from the training data set.

Reference is made to FIG. 1 exemplifying a method for generating a prediction model according to some embodiments of the present disclosure. As shown, the method utilizes an initial data set 1010 indicative of a plurality of spectrogram data pieces (S) obtained from a plurality of individuals, and respective blood biomarkers' data (B) of the same plurality of individuals 1020, typically obtained following analysis of a blood sample from the respective individuals. Spectrogram data is exemplified in FIG. 2A showing absorption levels for different wavelengths collected in a selected number of sampling instances. Data pieces, including spectrogram and respective biomarkers' data, are illustrated in FIG. 2B where the biomarkers' data is presented in a list of biomarkers ($b_n$) obtained by analysis of blood samples. Generally, each spectrogram data piece is collected from an individual using a reflection-based spectrometer directed at the individual's skin, e.g., on the wrist, or other places. While a complete near infrared (NIR) spectrogram may require about 1 second acquisition time, the spectrogram data pieces may include a selected number of spectrogram scans collected within a period of between 10 seconds and 2 minutes. This acquisition time is directed at blood circulation time through the patient's blood system. Additionally, each individual provides a blood sample that is taken to a laboratory to obtain blood analysis indicating desired blood biomarkers. Blood biomarker results (B) are collected and used to label the spectrogram data, providing a plurality of data pieces indicative of spectrogram data and respective blood biomarkers' data obtained from a plurality of individuals 1020.

The spectrogram data pieces may be pre-processed, or pre-treated, using one or more techniques such as baseline normalization, spectrum truncation, signal-to-noise ratio optimization, signal cleaning, spectrum derivation, band deletion, spectrum averaging, etc. Pre-processing of the spectrogram data pieces may be directed at reducing noise associated with measurement apparatus and movement, as well as defining spectral range between the entire data set. The pre-processing may be performed at the time of spectrogram collection and/or following collection of the entire data set. Further, the collected spectrograms may be assessed for noise levels and consistency. For example, spectrogram data pieces that are overly noisy, or are inconsistent (e.g., standard deviation above a selected threshold between instances of spectrograms collected from a single individual) may be disregarded and discarded, together with the respective blood biomarker data.

To improve prediction accuracy of the model, the present disclosure generally utilizes determining a selected number of groups of biomarkers 1030. The list of biomarkers for which the prediction model is directed may be any list of materials that may exist in a person's blood and may be a target for analysis. Such biomarkers may include for example: red blood cells count (RBC), hemoglobin, hematocrit, Mean Corpuscular Volume (MCV), Mean Corpuscular Hemoglobin (MCH), Mean Corpuscular Hemoglobin Concentration (MCHC), platelets, Mean Platelet Volume (MPV), Red blood cell distribution width (RDW), Absolute Neutrophils, Absolute Lymphocytes, Absolute Monocytes, Absolute Eosinophils, Absolute Basophils, Total Cholesterol, Triglycerides, Low Density Lipoprotein (LDL-C), High Density Lipoprotein (HDL-C), Glucose, Blood Urea Nitrogen, Creatinine, Sodium, Potassium, chloride, Carmon dioxide, Uric Acid, Albumin, Globulin, Calcium, Phosphorus, Alkaline Phosphatase, Alanine amino transferase (ALT or SGPT), Aspartate amino transferase (AST or SGOT), LDH, Total Bilirubin, GGT, Iron, TIBC, C-Reactive Protein, Cortisol, DHEA-Sulfate, Estimated Glomerular Filtration Rate (eGFR), Estradiol, Ferritin, Folate, Hemoglobin A1c, Homocysteine, Progesterone, Prostate Specific Ag (PSA), Testosterone, Thyroid-Stimulating Hormone, Vitamin D, or any other biomarkers that may be a target for biomedical analysis. From this list, the biomarkers may be separated into groups of two or more biomarkers selected in accordance with typical concentration levels, and/or level of effect of the biomarker on spectrogram data. Each biomarker may be characterized by typical amount present in a selected blood volume, and this amount may be weighted to indicate spectral absorbance effect of the biomarker. The biomarkers are arranged in groups including two or more biomarkers characterized by a high amount (concentration) and one or more biomarkers characterized by a low amount (concentration).

The various biomarkers are arranged in a selected number of groups, such that each group includes two or more (preferably three or more) biomarkers. Generally, selected, some or all of the biomarkers included in the model are placed in two or more groups each 1040.

According to some embodiments of the present disclosure, the biomarkers selected to take part in the models are arranged in groups in accordance with concentration levels, and/or level of expected effect of the biomarkers of spectroscopic analysis. More specifically, the biomarkers may be arranged into groups, where each group includes two or more biomarkers characterized by typical concentration levels above a first threshold, and one or more biomarkers characterized by typical concentration below a second threshold. In this connection it should be noted that the typical concentration levels are generally presented as average concentration of a biomarker in a wide population of individuals, rather than concentration in a single blood sample. Generally, concentration of the biomarkers may be determined as percentage of a typical blood sample composition, and may be weighted by general absorption levels indicating total effect on spectrogram data of the specific biomarkers. For example, RBC is present in blood samples at levels of 4-6 million cells per microliter. Additionally, high concentration biomarkers may include hemoglobin, sodium, glucose, etc. The high concentration level biomarkers are paired in groups together with selected low-concentration biomarkers, such as insulin, vitamin D, etc.

The biomarkers may be grouped in accordance with concentration levels, and/or the level of effect on spectrogram data of each biomarker, associated by the typical spectral effect of each biomarker. Such a typical spectral effect may be associated with a number of functional groups defining the chemistry of a material. Such functional groups are typically identified by NIR spectroscopy, and though they may be difficult to be directly identified in a biologically complex sample as blood, the use of a prediction model based on spectrogram data enhances prediction accuracy as a result of such grouping.

Generally, the concentration levels may be selected in accordance with a first concentration threshold, and possibly a second concentration threshold. In some configurations, biomarkers having a concentration (in particles per volume of blood sample) that exceeds the first threshold may be considered as having a high concentration. In some further embodiments, the first threshold may be indicative of 10% of blood composition, indicating high concentration.

Using the selected groups of biomarkers, the method according to some embodiments of the present disclosure includes training a prediction model to predict concentration levels of biomarkers of the various groups based on the data set 1050. The prediction model may utilize one or more chemometric algorithms, Artificial Intelligence, machine learning, and/or other statistical models, selected to predict a list of biomarkers in accordance with spectrographic data obtained from a patient. The technique of the present disclosure utilizes the provided data set including spectrogram (S) and respective blood biomarker data (B) for calibrating the prediction model in accordance with actual data obtained from a plurality of individuals. The prediction model may utilize determining one or more loss functions, associated with differences between biomarker data predicted by the model (Y) in accordance with input spectrogram data (S), and actual biomarker data (B) obtained from the individual providing the spectrogram data (S). To provide reliable results, the technique utilizes calibrating the prediction model to minimize loss function using a data set including a plurality of spectrogram and respective blood biomarkers data.

Generally, the prediction model may utilize further machine learning or Artificial Intelligence techniques, including, for example: Principal Component Analysis, Principal Component Regression, Partial Least Squares, Parallel Factor Analysis, N-way Partial Least Squares, Multiple Linear Regression, Hierarchical Cluster Analysis, K-nearest Neighbors, Support Vector Machines, Naïve Bayes, Linear or Normal Discriminant Analysis, Soft Independent Modeling of Class Analogy, Feedforward Neural Network, Recurrent Neural Network, Bayesian Regularization, Convolutional Neural Network, Generative Adversarial Network, or any other suitable prediction model configuration. Further, the prediction model may utilize a parallel or sequential chain of Artificial Intelligence techniques, chemometric techniques, and/or statistical modeling.

The prediction model according to some embodiments of the present disclosure may utilize one or more prediction routes. The different prediction routes are generally configured to receive similar input data, which may undergo several pre-processing variations, such as marking of selected wavelengths as having different weights, and are configured for processing of the input data to obtain output data associated with respective different target (loss) functions. As described herein below, different prediction routes may be configured to provide prediction data of different groups of biomarkers. The different prediction routes may operate in parallel or sequentially between them, and utilize one or more Artificial Intelligence, chemometric and/or statistical modeling techniques, as described above with reference to the prediction model.

In view of the plurality of groups of biomarkers, the prediction model may include a plurality of prediction routes, or sub-models, each prepared for predicting data on biomarkers of a selected group 1060. Accordingly, in some embodiments of the present disclosure, the method may include generating a prediction model including a selected number of prediction routes, each configured in accordance with a respective group of the biomarkers of the selected number of groups. As indicated above, at least some of the biomarkers, generally selected based on importance in medical diagnosis, or all the biomarkers, are included in two or more groups. This group selection provides a plurality of prediction routes for the biomarkers that present in two or more groups, and thus enhances prediction accuracy with respect to techniques that aim to predict a single biomarker at a time, or techniques that aim to predict a complete list of biomarkers simultaneously.

Following training of the prediction model, typically in the form of a selected number of sub-models of prediction routes, the method according to some embodiments of the present disclosure provides output data indicative of a trained prediction model 1070. The output data may be generated in the form of computer readable code that may be stored in a computer readable medium, and, when executed by one or more processors, enables prediction of biomarkers in response to input data in the form of one or more spectrogram data of a patient. As indicated above, the prediction model may be in the form of a plurality of prediction routes, each providing prediction output indicative of biomarkers in a respective group of biomarkers. The output prediction model may also include computer readable instructions indicative of determining a format for output data on biomarkers that are included in a number of groups.

Figure 3:
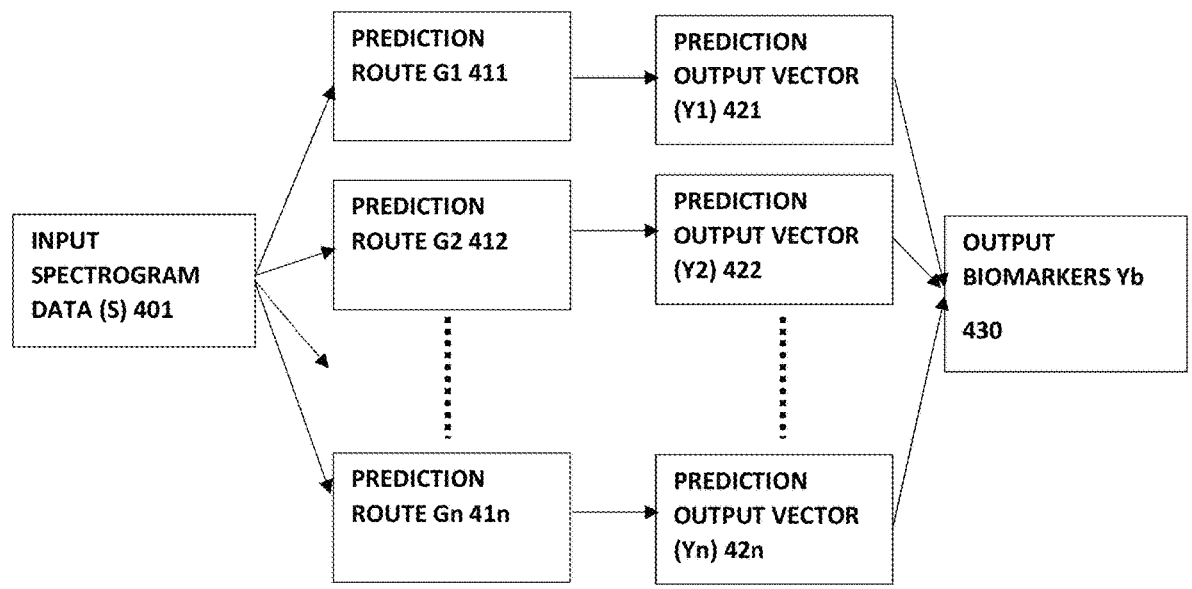
FIG. 3 illustrates a general operation process of a prediction model according to some embodiments of the present disclosure.

An illustration of operation of the prediction model according to some embodiments of the present disclosure is shown in FIG. 3. As shown, input spectrogram data (S) 401 is provided as input data to a plurality of prediction routes 411-41n, each configured to provide output data 421-42n indicative of prediction of a selected group of biomarkers (Y1-Yn). The prediction model also includes instructions for determining output data indicative of biomarkers (Y1-Yn) 430.

Generally, the prediction data (Y1-Yn) may be in the form of a function indicating concentration of the respective group of biomarkers in accordance with one or more spectral values of spectrogram data. Accordingly, for each group of biomarkers the respective prediction data (Y1-Yn) can be used to determine an output list of biomarker concentration data (Yb). For example, given a certain biomarker being predicted by two or more prediction routes, i.e., a biomarker included in two or more groups, the output concentration of that biomarker may be determined by averaging the predicted concentration output of each of the respective prediction routes, including a reference to ranging of the two or more different predictions as error margins. In some embodiments, the output concentration of such a biomarker may be determined by weighted average of the different prediction routes' output, using respective accuracy measures such as weights, such that prediction routes having higher accuracy contribute to output concentration of such biomarkers more than prediction routes characterized by lower accuracy levels. As indicated herein, the weights between prediction of a specific biomarker by different prediction routes may be determined by relative accuracy of each of the respective prediction routes.

Figure 4:
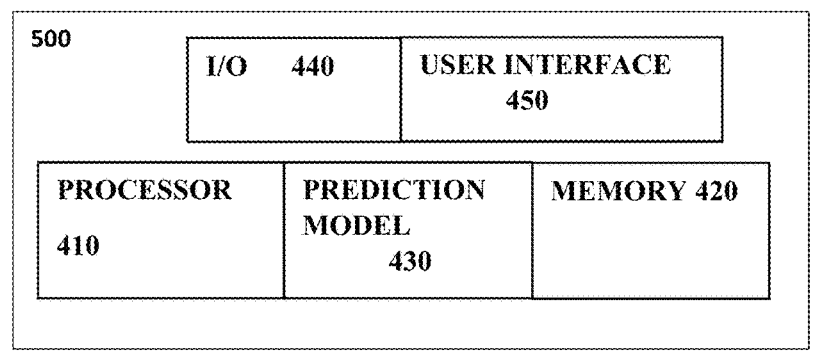
FIG. 4 schematically illustrates a system configured for generating a prediction model according to some embodiments of the present disclosure.
Figure 5:
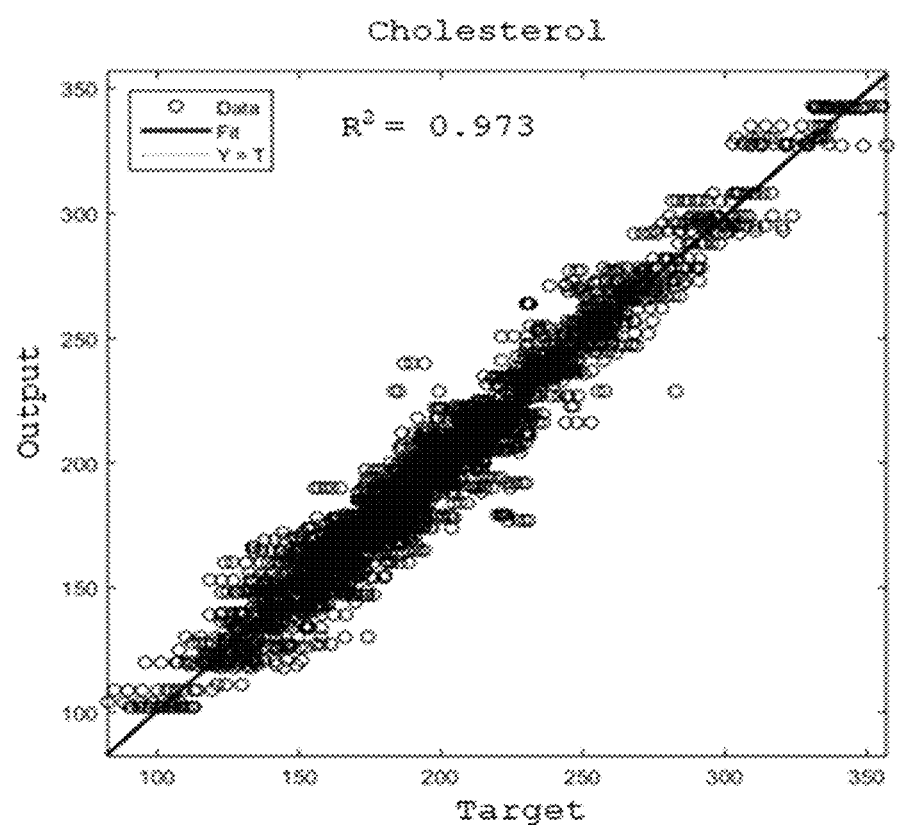
FIG. 5 exemplifies correlation factor $R^2$ indicative of prediction accuracy for cholesterol concentration determined based on an input data set.

As indicated above, the method according to some embodiments of the present disclosure may be implemented using one or more processors and memory circuitry. FIG. 4 illustrates a computer-based system 400 for generating one or more prediction models in accordance with some embodiments of the present disclosure. System 400 includes at least one processor 410 and memory 420, typically defined as processor memory circuitry (PMC). The system 400 also includes suitable input and output communication module 440, and may include user interface 450, e.g., including display, keyboard etc. The PMC is operative to implement one or more algorithms suitable for generating data indicative of the at least one prediction model 430 in accordance with the technique described herein. In some additional embodiments described herein below, the PMC may be configured to implement at least one prediction model 430 in accordance with input data indicative of one or more spectrograms collected from an individual's tissue, to provide output data indicative of a selected list of biomarkers. In particular, the processor can execute several computer-readable instructions implemented on a computer-readable memory stored or comprised in the PMC, wherein execution of the computer-readable instructions enables data processing of input data in the form of spectrogram data labelled by biomarker data for determining prediction model parameters. In some additional embodiments the PMC may implement computer readable instructions for processing input data indicative of a spectrogram for operating one or more prediction models, and generate output data indicative of predicted biomarker concentration in a respective individual's blood.

Referring back to FIG. 1, operation of training one or more prediction models may include a first calibration stage, a second validating stage, and a third testing stage. Generally, each prediction route may be processed for the respective group of biomarkers separately to minimize the respective loss function. The first calibrating stage includes performing an initial optimization of a selected prediction route to minimize the determined loss function. The calibration stage may utilize a first portion of the data set, herein referred to as calibration data set. The calibration stage may utilize one or more prediction model training techniques, such as stochastic gradient descent, or any other suitable training technique for prediction models, to bring the predicted output (Y) for each input spectrogram (S) closer to the respective blood biomarkers data (B).

The second validation stage may be performed using a second portion of the data set. For each prediction route, accuracy of the predicted output (Y) is validated with respect to the actual blood biomarkers data (B) using data pieces of the second portion of the data set. The validation stage may include further optimization of the prediction route to minimize the respective loss model. Following validation stage, data indicative of the loss function may be processed in accordance with a respective threshold associated with expected results. If the prediction accuracy is insufficient, the first and second portions of the data set may be reshuffled, and re-split, and the calibration and validation stages may be repeated. In some configurations, specifically following insufficient accuracy determined following testing of the prediction model, an additional training data set may be required. In this case, the system, e.g., using the computer processor of the PMC (as defined herein below) may generate an output signal requesting an additional data set.

The third testing stage includes testing of the prediction model accuracy on a third portion of the data set. The testing stage may generally avoid further optimization of the prediction model, and directly test accuracy thereof using input data (S) and target output (B) that was not used in the calibration and validation stages. If the prediction accuracy of output data (Y) is insufficient, in accordance with a selected threshold, an additional reference data set, in the form of spectrogram data (S) and blood biomarker data (B) may be requested, and calibration and validation stages may be repeated using the existing and additional data.

Generally, in some embodiments, an accuracy measure may be associated with a correlation value for each specific biomarker. In some embodiments, the correlation values may be the statistical coefficient of determination, also known as $R^2$. In this connection, reference is made to FIG.

5 exemplifying correlation factor $R^2$ for cholesterol determined based on an input data set. Generally, to provide an accurate prediction, the accuracy measure is preferred to be sufficiently high, i.e., closer to unity. However, as the prediction model of the present disclosure is generally directed at predicting a plurality of biomarkers that are generally not directly correlated, the accuracy measure $R^2$ is preferred to be lower than one, to allow certain flexibility due to variations between individuals, and specifically to avoid overfitting to the training data set. Accordingly, in some embodiments, sufficient accuracy at the validation stage may be determined within the range of $R^2$ between 0.70 and 0.99. Further, at the testing stage, sufficient accuracy may be determined based on $R^2$ in the range between 0.65 and 0.99. Typically, the selected ranges may vary in accordance with size of the data set and clinical relevance of the blood biomarkers. As indicated above, if correlation value for at least one biomarker within a group is outside the desired range, the respective prediction route may be retrained by repeating calibration and validation stages following a shuffled data set.

The present technique was used for generating a prediction model based on exemplary data set of spectrogram and blood biomarker data. The first portion of the data used for calibration of the prediction model includes 60% of the data set. The validation and testing stages using second and third portions of the data set were split into 20% of the data pieces each. For completeness, additional prediction models were generated for each specific biomarker, one-by-one, and for the entire set of biomarkers combined.

Accuracy measures of the so-generated prediction models are summarized in table 1 below. The correlation values ($R^2$) presented for each method are the average of all $R^2$ values for prediction of the different biomarkers. As shown, initial accuracy for prediction of each biomarker separately was higher, obtained following calibration and validation. However, when handling new input data in the testing stage, grouping biomarkers into groups, and defining prediction routes for each group of biomarkers, provides increased accuracy.

TABLE 1

| Method | Calibration phase ($R^2$) $S_C$-$B_C$ | Validation phase ($R^2$) $S_V$-$B_V$ | Testing phase ($R^2$) $S_T$-$B_T$ |
| --- | --- | --- | --- |
| One-by-one | 0.965 | 0.932 | 0.613 ± 0.227 |
| All together | 0.867 | 0.860 | 0.511 ± 0.196 |
| With grouping | 0.950 | 0.917 | 0.872 ± 0.182 |

It should be noted that the accuracy measures obtained at calibration and validation stages are based on input data used for optimization of the calibration model. Accordingly, although initial accuracy during optimization may seem better for prediction of biomarkers one-by-one, actual prediction accuracy is measured with respect to new input data at the testing stage.

Figure 6:
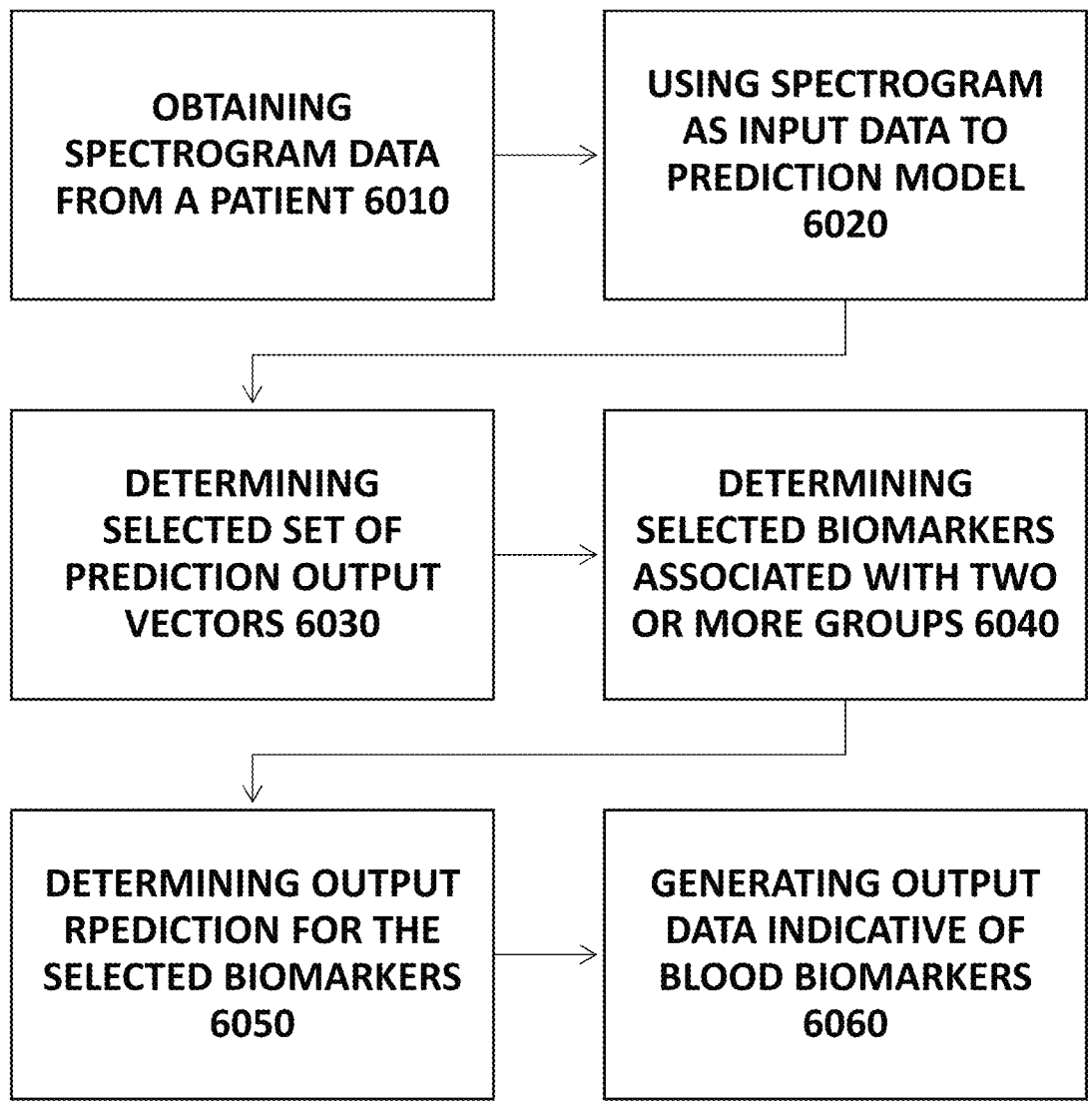
FIG. 6 illustrates a method for non-invasive determination of blood biomarkers according to some embodiments of the present disclosure.

Following generating of a prediction model as described above, the present disclosure provides a method for determining blood biomarkers data of a patient. As indicated, the method according to some embodiments of the present disclosure is non-invasive, and requires spectrometric measurement obtained from the tissue of a patient. Such tissue may generally and preferably be skin tissue such as from the wrist, hand, neck, forehead, fingertip, etc. The spectrogram data may be obtained by any selected spectrometer having a spectral range including near infrared spectrum, as defined above. FIG. 6 exemplifies a method for determining blood biomarkers according to some embodiments of the present disclosure. As shown, the method includes obtaining spectrogram data from a patient 6010. The spectrogram data may be directly obtained from the patient at a clinic or obtained at a remote clinic and transmitted via wired or wireless communication. In some embodiments, the method may operate for processing pre-obtained spectrogram data stored in a storage unit in the form of digital data. The spectrogram data may include one or more readouts collected within a selected timeframe from the user. Generally, obtaining a plurality of spectrometric readouts within a timeframe of 1-5 minutes may provide enhanced data following complete blood circulation of the patient.

To determine blood biomarker data, the method includes providing the spectrogram data to the prediction model 6020. The prediction model may be pre-stored in a computer readable medium and executed by one or more processors as exemplified in FIG. 4 above. In operation, the prediction model may operate using a selected set of prediction routes, each associated with respective processing operations and providing a respective prediction output vector 6030 indicating predicted concentration values of a group of biomarkers.

Within the different output prediction vectors, the method may include classifying one or more biomarkers initially selected, into two or more groups 6040. Predicted concentration of these biomarkers is provided within two or more prediction vectors, and the predicted concentration may slightly vary between the different vectors. Accordingly, for these biomarkers, the method may include determining an output prediction concentration 6050. The concentration values may be determined by averaging concentration values of the two or more prediction vectors, by regular or weighted averaging, as indicated above. Further, output data including predicted concentration of a list of requested biomarkers can be provided 6060, optionally including selected margins in accordance with operation of the prediction models and/or averaging operations.

Figure 7:
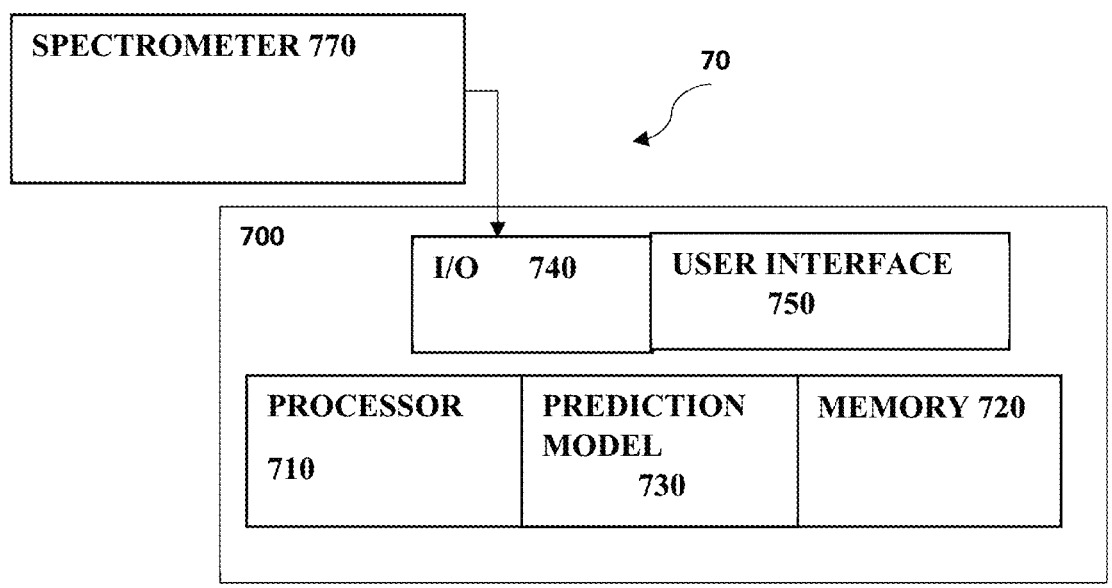
FIG. 7 exemplifies a system for non-invasive determination of blood biomarkers according to some embodiments of the present disclosure.

FIG. 7 illustrates a system 70 for non-invasive determination of blood biomarkers of a patient. The system 70 generally includes a computer-based system 700 including at least one processor 710 and memory 720, typically defined as processor memory circuitry (PMC), and may also include a spectrometer 770 configured to measure absorption levels in a selected spectral range, e.g., generally including 600-2700 nm from a user's tissue such as skin, as described above. The computer-based system 700 also includes suitable input and output communication module 740 for receiving input spectrogram data from the spectrometer when used, and may include user interface 750, e.g., including display, keyboard etc. The PMC is pre-stored with computer readable data indicative of one or more prediction models, as described above, and operational instructions for implementing the prediction model 730 based on input data in the form of spectrogram data. In particular, the processor can execute several computer-readable instructions implemented on a computer-readable memory stored or comprised in the PMC, wherein execution of the computer-readable instructions enables data processing of input data in the form of spectrogram data labelled by biomarker data for determining prediction model parameters. In some additional embodiments the PMC may implement computer readable instructions for processing input data indicative of spectrogram for operating one or more prediction models, and generate output data indicative of predicted biomarker concentration in a respective individual's blood.

Generally, it should be noted that the system 70 is illustrated herein in combination with a spectrometer 770 for clarity. Generally, the system 70 may be operable as a computer-based system and obtain patient spectrogram data via a communication link from a selected storage unit for non-invasively determining data on blood biomarkers at a remote location.

Figure 8A:
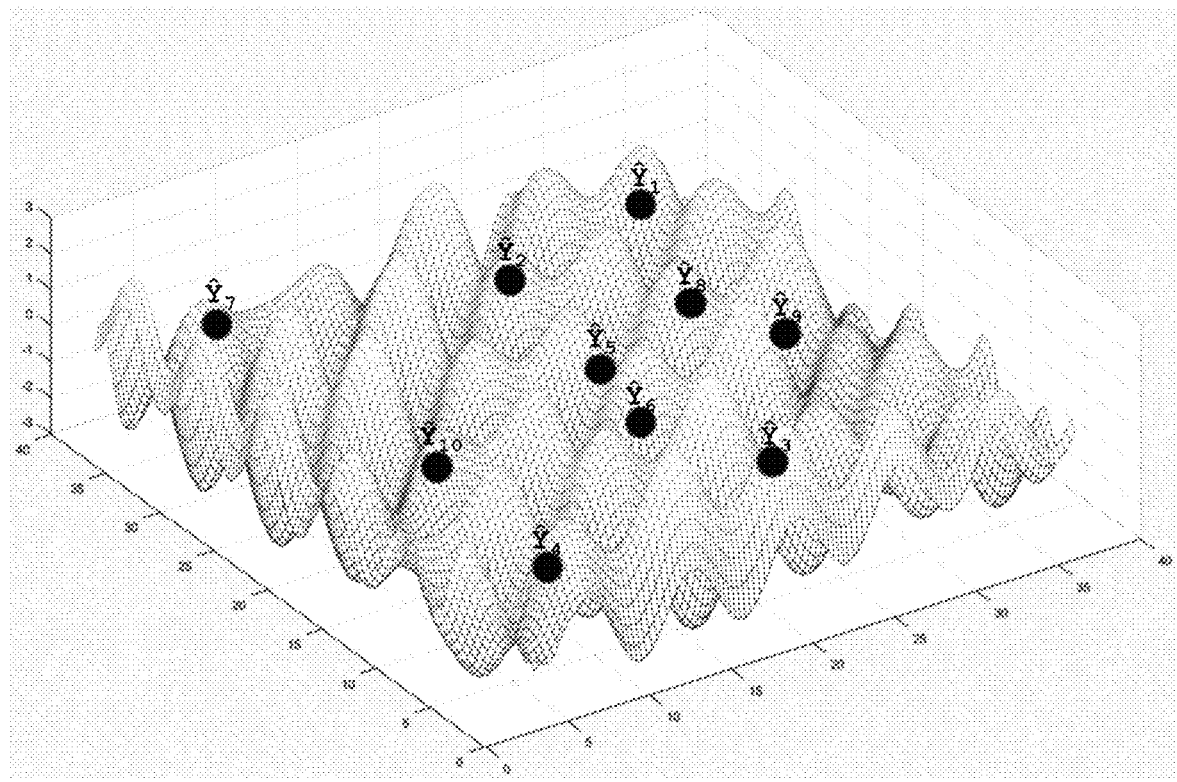
FIGS. 8A to 8D exemplify prediction optimization according to some embodiments of the present disclosure with respect to conventional techniques.
Figure 8B:
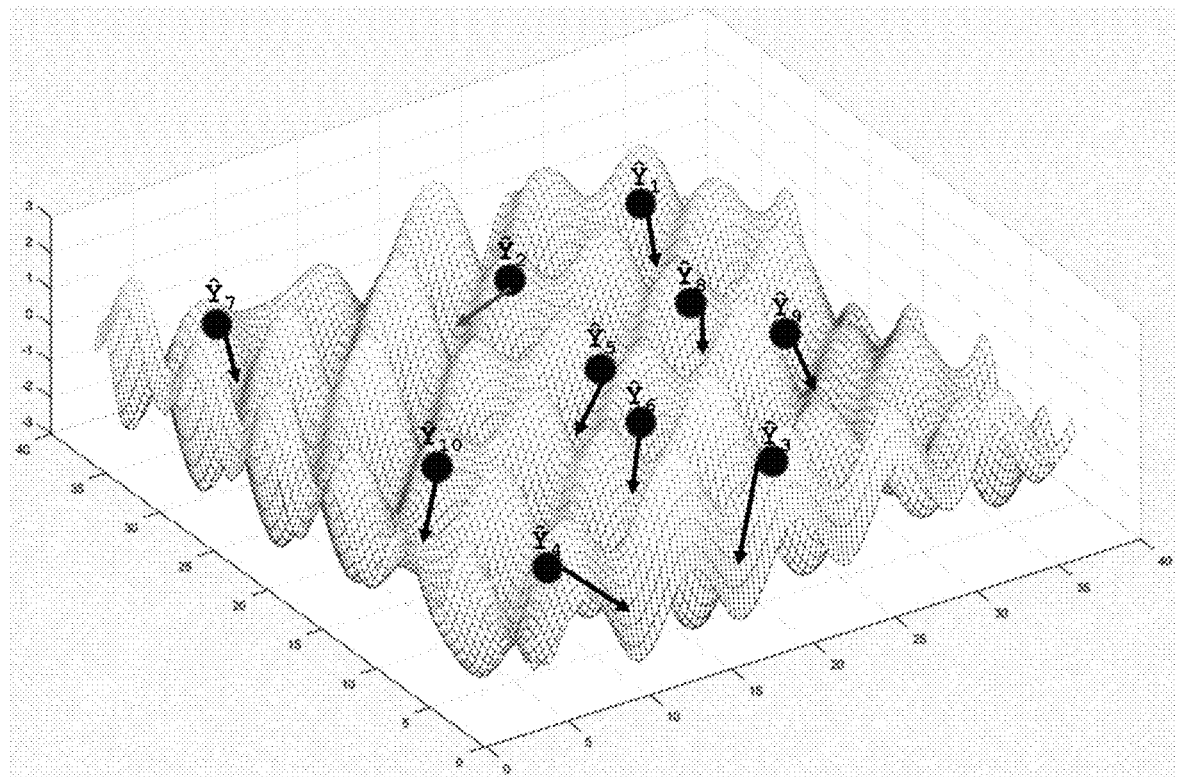
Figure 8C:
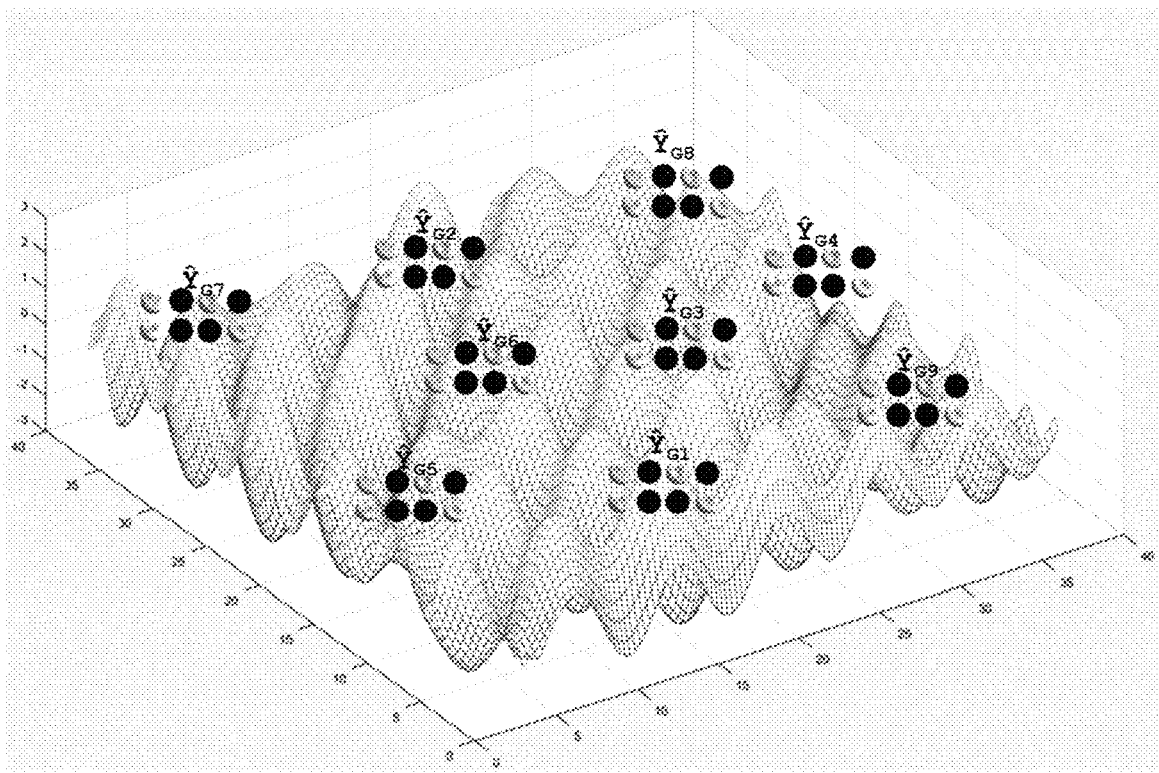
Figure 8D:
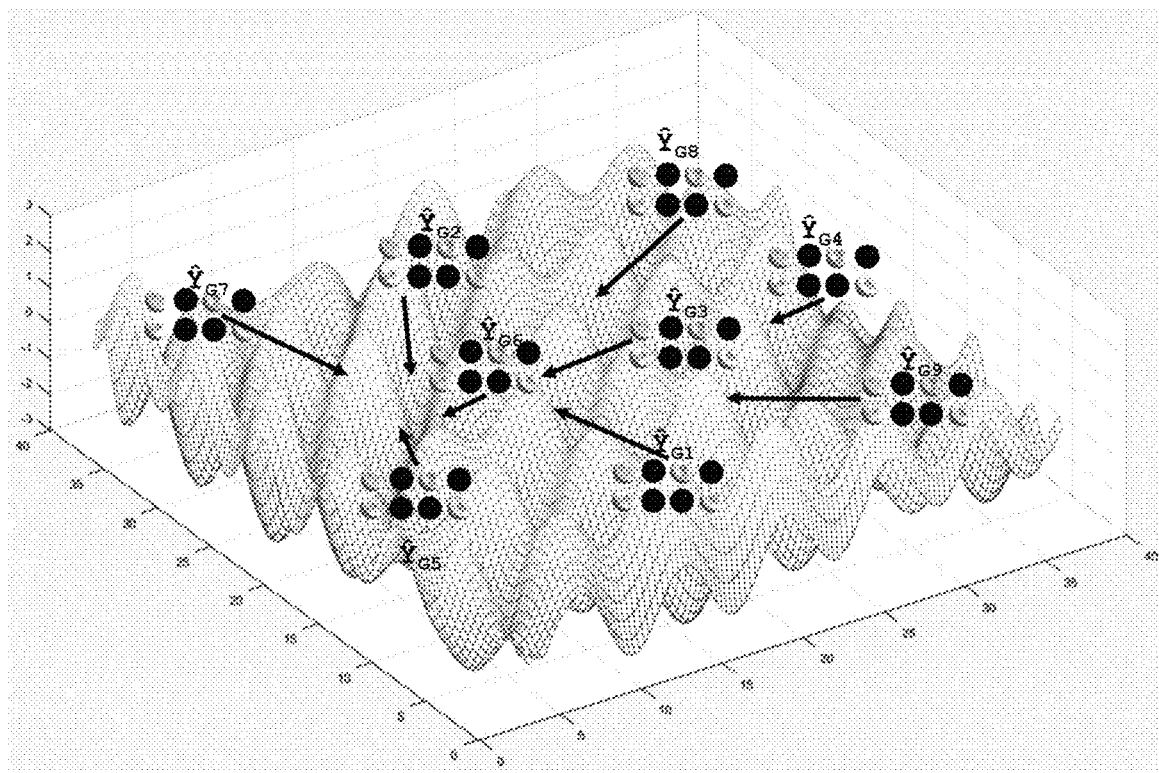

As indicated above, the present disclosure utilizes grouping of target biomarkers in accordance with preselected characteristics. This enables the present technique to provide improved prediction accuracy. Reference is made to FIGS. 8A to 8D illustrating an optimization process for a prediction model and exemplifying the advantage of the present technique. FIGS. 8A and 8B illustrate respectively certain prediction solutions utilizing a plurality of prediction solutions $\hat{Y}_1$ to $\hat{Y}_{10}$, each associated with a single biomarker, and expected convergence following further optimization steps. FIGS. 8C and 8D illustrate, respectively, prediction solutions $\hat{Y}_{G1}$ to $\hat{Y}_{G9}$ for a number of groups of biomarkers and expected convergence following optimization steps.

Generally, the dispersion of prediction solutions illustrated in FIG. 8A for prediction of biomarkers one-by-one has similar characteristics to the solution dispersion associated with prediction of the entire set of biomarkers together. In both cases, the level of data variability is sufficiently high, resulting in over-fitting of the prediction to the data provided for training, such that the final solution does not converge with new input.

Alternatively, the present technique utilizes optimization of selected sets of groups of biomarkers. This technique maintains a small number of local optima, and similarity in characteristics of the different biomarkers results in several groups converging together.

According to some embodiments of the present disclosure the groups of biomarkers are established based on typical concentration thereof. Thus, blood biomarkers associated with typical higher concentration act as "mathematical catalysts" of the blood markers with typical lower concentration values. Generally, and as may be observed in the area of spectroscopy, molecules present at lower concentrations have signals that are less noticeable, sometimes being confused with noise. Using blood markers at higher concentrations will allow for easier quantification of these blood markers, through convergence of optima during application of the loss function, such as may be seen in FIGS. 8C and 8D. Since the blood markers with high concentration must have substantially high values, it will force the loss function to only converge on the optima that present values that are substantially high for those blood markers. The blood markers that present lower concentration levels will therefore have values that will match the signals of the matrix of spectra S and the real concentration of said blood marker in vector B.

As indicated above, the present technique may be implemented by one or more computer systems using respective one or more processors and memory circuitries. The system may be directly connected to a spectrometer for providing on-the-spot blood biomarkers data, or positioned in a selected location to provide network processing and/or offline biomarker prediction processing.

It is to be noted that the various features described in the various embodiments can be combined according to all possible technical combinations.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based can readily be utilized as a basis for designing other structures, methods, and systems for carrying out the several purposes of the presently disclosed subject matter.

Those skilled in the art will readily appreciate that various modifications and changes can be applied to the embodiments of the invention as hereinbefore described without departing from its scope, defined in and by the appended claims.

The invention claimed is:

1. A method for determining levels of blood biomarkers implemented by a processor and memory circuitry (PMC), comprising:
   (a) providing near infra-red spectrogram data of a patient's living tissue;
   (b) using one or more pre-trained prediction models comprising a selected number of prediction routes for processing the near infra-red spectrogram data, and determining accordingly prediction data on a selected group of biomarkers;
   (c) determining one or more biomarkers associated with a number of groups, and determining for the one or more biomarkers an average concentration data of said one or more biomarkers in accordance with output data of a number of prediction routes associated with said number of groups; and
   (d) generating output data indicative of estimated levels of a selected set of biomarkers for said patient.

2. The method of claim 1, wherein said providing spectrogram data comprises providing spectrogram data in a range between 600 nm and 2700 nm.

3. The method of claim 1, wherein said providing spectrogram data comprises obtaining a spectrometric reading of said patient's skin.

4. The method of claim 1, wherein said selected number of prediction routes comprises prediction routes pre-trained for predicting data on selected groups of biomarkers, being different between said prediction routes.

5. The method of claim 4, wherein said selected groups of biomarkers comprise a selected number of groups, each group comprising two or more biomarkers characterized by typical concentration above a first threshold, and one or more biomarkers characterized by typical concentration below a second threshold.

6. A program storage device readable by machine, tangibly embodying a program of instructions executable by the machine to perform a method for determining levels of blood biomarkers, comprising:
   (a) providing spectrogram data indicative of near infra-red absorption of a patient's tissue;
   (b) using one or more pre-trained prediction models comprising a selected number of prediction routes for processing the spectrogram data, and determining prediction data on a selected group of biomarkers accordingly;
   (c) determining one or more biomarkers associated with a number of groups and for the one or more biomarkers associated with a number of groups, determining an average concentration data of in accordance with the prediction data of a number of prediction routes associated with said number of groups; and
   generating output data indicative of estimated levels of a selected set of biomarkers for said patient.

7. The program storage device of claim 6, wherein said selected groups of biomarkers comprise a selected number of groups, each group comprising two or more biomarkers characterized by typical concentration above a first threshold, and one or more biomarkers characterized by typical concentration below a second threshold.

8. A computer program product comprising a computer useable medium having computer readable program code embodied therein for determining levels of blood biomarkers, the computer program product comprising:
   computer readable program code for causing the computer to provide spectrogram data indicative of near infra-red absorption of a patient's tissue;
   computer readable program code for causing the computer to use one or more pre-trained prediction models comprising a selected number of prediction routes to process the spectrogram data and to determine prediction data on a selected group of biomarkers;
   computer readable program code for causing the computer to determine one or more biomarkers associated with a number of groups and to determine an average concentration data of said one or more biomarkers in accordance with the prediction data being output of a number of prediction routes associated with said number of groups; and
   computer readable program code for causing the computer to generate output data indicative of estimated levels of a selected set of biomarkers for said patient.

9. The computer program product of claim 8, wherein said selected groups of biomarkers comprise a selected number of groups, each group comprising two or more biomarkers characterized by typical concentration above a first threshold, and one or more biomarkers characterized by typical concentration below a second threshold.

10. A system for non-invasive determining of levels of blood biomarkers comprising:
    a processor and memory circuitry (PMC), wherein the PMC comprises a pre-stored prediction model, and is configured to:
    (a) obtain spectrogram data indicative of near infra-red absorption of a patient's tissue;
    (b) use one or more pre-trained prediction models comprising a selected number of prediction routes comprising prediction routes pre-trained for predicting data on selected groups of biomarkers, being different between said prediction routes, and determining prediction data on a selected group of biomarkers;
    (c) determine one or more biomarkers associated with a number of groups and determine for each of the one or more biomarkers an average concentration data of said one or more biomarkers in accordance with the prediction data being output of a number of prediction routes associated with said number of groups; and
    (d) generate output data indicative of estimated levels of a selected set of biomarkers for said patient.

11. The system of claim 10, further comprising at least one spectrometer connectable to said PMC for transmission of communication signals, said at least one spectrometer being configured for obtaining spectrogram data from biological tissue.

12. The system of claim 11, wherein said at least one spectrometer is configured to obtain spectrogram data from a skin portion of an individual.

13. The system of claim 11, wherein said at least one spectrometer is configured to obtain spectrogram data comprising a spectral range between 600 nm and 2700 nm.

14. The system of claim 10, wherein said selected number of prediction routes comprise prediction routes pre-trained for predicting data on a selected groups of biomarkers, being different between said prediction routes.

15. The system of claim 14, wherein said selected groups of biomarkers comprise a selected number of groups, each group comprising two or more biomarkers characterized by typical concentration above a first threshold, and one or more biomarkers characterized by typical concentration below a second threshold.

* * * * *